United States Patent [19] [11] 4,213,978
Bodor et al. [45] Jul. 22, 1980

[54] ANTI-ACNE AND ANTI-SEBORRHEA PRODRUG DERIVATIVES OF PROGESTERONE

[75] Inventors: Nicholas S. Bodor, Lawrence; Kenneth B. Sloan, Eudora, both of Kans.

[73] Assignee: INTERx Research Corporation, Lawrence, Kans.

[21] Appl. No.: 966,585

[22] Filed: Dec. 5, 1978

Related U.S. Application Data

[63] Continuation-in-part of Ser. No. 886,589, Mar. 14, 1978.

[51] Int. Cl.² .................. A61K 31/58; C07J 17/00
[52] U.S. Cl. .................. 424/241; 260/239.5
[58] Field of Search .................. 260/239.5; /Steroids MS File

[56] References Cited

U.S. PATENT DOCUMENTS

| 3,309,362 | 3/1967 | Meyer et al. | 260/239.5 |
| 4,069,322 | 1/1978 | Bodor et al. | 260/239.5 |

Primary Examiner—Elbert L. Roberts
Attorney, Agent, or Firm—Burns, Doane, Swecker & Mathis

[57] ABSTRACT

Transient, topically active thiazolidine type prodrug forms of progesterone are disclosed.

41 Claims, No Drawings

ANTI-ACNE AND ANTI-SEBORRHEA PRODRUG DERIVATIVES OF PROGESTERONE

CROSS-REFERENCE TO RELATED APPLICATIONS

This application is a continuation-in-part of U.S. Pat. application Ser. No. 886,589, filed Mar. 14, 1978.

BACKGROUND OF THE INVENTION

1. Field of the Invention

The present invention relates to certain selected transient prodrug forms of progesterone and related compounds useful in the treatment of acne and seborrhea.

For purposes of this specification, the term "prodrug" denotes a derivative of a known and proven prior art steroid compound [i.e., progesterone or a related compound] which derivative, when administered to a warm-blooded animal, "cleaves" in such a manner as to release the proven drug at its target site or sites of activity.

The term "transient" denotes enzymatic and/or chemical hydrolytic "cleavage" of the compounds of the instant invention in a manner such that the proven drug form [e.g., progesterone] is released, while the remaining "cleaved" moiety remains nontoxic and is metabolized in such a manner that nontoxic, metabolic products are produced.

Finally, the term "pharmaceutically acceptable acid addition salt" as used herein generally includes the nontoxic acid addition salts of selected compounds of formula [I], formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, sulfonic, toluenesulfonic, and the like.

2. Description of the Prior Art

Acne is a common disorder of the skin, especially prevalent during adolescence, characterized by the accumulation of sebum in the sebaceous ducts resulting from obstruction of the ducts and increased secretion of sebum. Studies have indicated that 5α-dihydrotestosterone (5α-DHT) a metabolite of testosterone, stimulates the sebaceous glands, and is found in the skin of acne patients in much greater amounts than in normal skin. Thus, a substance able to inhibit 5α-reductase would presumably prevent the 5α-reduction of testosterone to 5α-DHT and resultant stimulation of the sebaceous glands.

Progesterone, a 5α-reductase inhibitor, has recently been found to be effective in the topical treatment of acne cases, especially in cases in which hypersecretion of the sebaceous gland is the dominant factor. [Drug Intelligence and Clinical Pharmacy, Volume 12, March, 1978, pp. 151–7.] However, progesterone suffers from a serious disadvantage in that it undergoes rapid metabolic deactivation after topical administration. Thus, very large doses of progesterone must be administered to provoke a response and the duration of activity is nevertheless quite short.

In view of the foregoing, it is apparent that a serious need exists for a class of novel progestins which will overcome the aforementioned inefficiencies. That need is fulfilled by the subject steroidal prodrugs which are topically active and are not rapidly metabolically deactivated, but which are transient and which will cleave upon administration to the active parent steroid resulting in therapeutic concentrations and eliciting, albeit more efficiently and prolongedly, the same pharmacodynamic effect as would be elicited upon administration of the known parent natural or synthetic progestin.

SUMMARY OF THE INVENTION

It is one object of the present invention to provide prodrug forms of certain natural and synthetic progestins, which prodrugs, or transient derivatives, possess the capability of efficiently penetrating the biological barrier of the skin and which transient derivatives protect their respective parent molecules from rapid metabolic deactivation.

Another object of this invention is to provide certain steroidal prodrugs which will cleave following administration to the active parent steroid, in therapeutic concentrations.

Yet another object of the invention is to provide certain steroidal prodrugs which are well absorbed and which elicit the pharmacodynamic responses of their parent molecules in a more efficient and more prolonged action upon topical administration.

Still another object of the invention is to provide a new class of anti-acne and anti-seborrhea agents.

Another object of the invention is to provide certain steroidal prodrugs of progesterone and related compounds, that not only are completely dissolved at the absorption site and are prevented from premature metabolism-conjugation during absorption, but also afford in vivo recovery of the basic hormone in the optimum fashion to exert its activity.

It is another object of the present invention to provide such prodrug forms of conventional progestational steroids which, following administration, will "cleave" in such a manner as to enable the original parent steroidal moiety [i.e., progesterone, medroxyprogesterone acetate, hydroxyprogesterone caproate or haloprogesterone] to be released at its therapeutic site or sites of activity and to further permit the cleaved moiety(ies) unassociated with the parent steroidal moiety to be metabolized in a nontoxic fashion.

All the foregoing objects are achieved by topically administering to a subject afflicted with acne or seborrhea, a therapeutically effective anti-acne or anti-seborrhea amount of a compound having the structural formula:

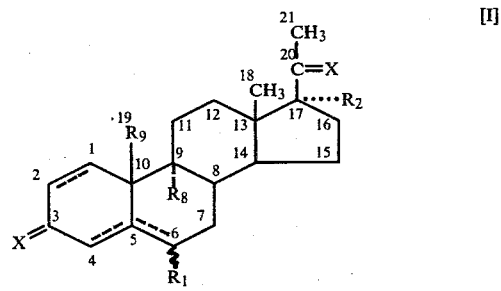

wherein each X is O or

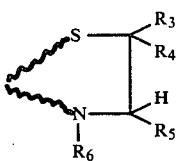

with the proviso that both X's cannot at the same time be 0, albeit either one or both can comprise the depicted thiazolidine nucleus;

$R_1$ is H, $C_1$–$C_8$ alkyl or halogen [e.g., Cl, F, or Br];

$R_2$ is H, OH, $OOCR_7$, halogen or $C_1$–$C_{10}$ alkyl;

$R_3$ and $R_4$ may be the same or different and each is H or $C_1$–$C_8$ alkyl;

$R_5$ is —$COOR_7$;

$R_6$ is H, —$COR_7$ or —$COOR_7$, with the proviso that, when $R_6$ is H, the pharmaceutically acceptable acid addition salts, HQ, of the compounds of formula [I] are also intended;

$R_7$ is H, $C_1$–$C_{20}$ alkyl, $C_2$–$C_{20}$ alkenyl, $C_5$–$C_7$ cycloalkyl, $C_5$–$C_7$ cycloalkyl-aryl (having from 6 to 10 carbon atoms), phenyl or $C_1$–$C_4$ alkyl substituted phenyl;

$R_8$ is H, Cl or F; and $R_9$ is H or $C_1$–$C_8$ alkyl.

In the compounds of the above formula [I], the bond between $C_1$ and $C_2$ is either a single or double bond. There is a double bond at either $C_4$–$C_5$ or $C_5$–$C_6$. Where $X \neq O$ in the 3-position, the $C_4$–$C_5$ double bond sometimes migrates to $C_5$–$C_6$.

A preferred group of compounds encompassed by formula [I] above consists of the compounds wherein the 1,2-linkage is saturated, $R_1$, $R_2$ and $R_8$ are each a hydrogen atom, and $R_9$ is a methyl radical, i.e. the pro-drugs of progesterone.

DETAILED DESCRIPTION OF THE INVENTION

While all of the compounds encompassed within generic formula [I] above essentially satisfy the objectives of the invention, nevertheless, certain selected compounds as are set forth immediately below, remain preferred:

[1] 5-Pregnene-3,20-dispiro-2'-di(1',3'-thiazolidine-4'-ethyl carboxylate);

[2] 5-Pregnene-3,20-dispiro-2'2'-di(1',3'-thiazolidine-4'-butyl carboxylate);

[3] 5-Pregnene-3,20-dispiro-2',2'-di(1',3'-thiazolidine-4'-hexyl carboxylate);

[4] 5-Pregnene-3,20-dispiro-2',2'-di(1',3'-thiazolidine-4'-decyl carboxylate);

[5] 5-Pregnene-3,20-dispiro-2',2'-di(1',3'-thiazolidine-4'-t-butyl carboxylate);

[6] 5-Pregnene-3,20-dispiro-2',2'-di(1',3'-di(1',3'-thiazolidine-4'-benzyl carboxylate);

[7] 5-Pregnene-3,20-dispiro-2',2'-di(1',3'-thiazolidine-4'-i-propyl carboxylate);

[8] 5-Pregnene-3-spiro-2'-(1',3'-thiazolidine-4'-ethyl carboxylate)-20-one;

[9] 5-Pregnene-3-spiro-2'-(1',3'-thiazolidine-4'-butyl carboxylate)-20-one;

[10] 5-Pregnene-3-spiro-2'-(1',3'-thiazolidine-4'-hexyl carboxylate)-20-one;

[11] 5-Pregnene-3-spiro-2'-(1'-3'-thiazolidine-4'-decyl carboxylate)-20-one;

[12] 5-Pregnene-3-spiro-2'-(1',3'-thiazolidine-4'-t-butyl carboxylate)-20-one;

[13] 5-Pregnene-3-spiro-2'-(1'-3'-thiazolidine-4'-benzyl carboxylate)-20-one;

[14] 5-Pregnene-3-spiro-2'-(1',3'-thiazolidine-4'-propyl carboxylate)-20-one;

[15] 5-Pregnene-3,20-dispiro-2',2'-di(1',3'-thiazolidine-5',5'-dimethyl-4'-ethyl carboxylate);

[16] 5-Pregnene-3,20-dispiro-2',2'-di(1',3'-thiazolidine-5',5'-dimethyl-4'-hexyl carboxylate);

[17] 5-Pregnene-3,20-dispiro-2',2'-di(1',3'-thiazolidine-5',5'-dimethyl-4'-butyl carboxylate);

[18] 6α-Chloro-5-pregnene-3,20-dispiro-2',2'-di(1',3'-thiazolidine-4'-ethyl carboxylate);

[19] 6α-Chloro-5-pregnene-3,20-dispiro-2',2'-di(1',3'-thiazolidine-4'-butyl carboxylate);

[20] 6α-Chloro-5-pregnene-3,30-dispiro-2',2'-di(1',3'-thiazolidine-4'-hexyl carboxylate);

[21] 6α-Methyl-17α-acetyloxy-5-pregnene-3,20-dispiro-2',2'-di(1', 3'-thiazolidine-4'-ethyl carboxylate);

[22] 6α-Methyl-17α-acetyloxy-5-pregnene-3,20-dispiro-2',2'-di(1', 3'-thiazolidine-4'-butyl carboxylate);

[23] 6α-Methyl-17α-acetyloxy-5-pregnene-2,30-dispiro-2',2'-di(1', 3'-thiazolidine-4'-hexyl carboxylate);

[24] 9α-Fluoro-17α-acetyloxy-5-pregnene-3,20-dispiro-2',2'-di(1', 3'-thiazolidine-4'-ethyl carboxylate);

[25] 9α-Fluoro-17α-acetyloxy-5-pregnene-3,20-dispiro-2',2'-di(1', 3'-thiazolidine-4'-butyl carboxylate);

[26] 9α-Fluoro-17α-acetyloxy-5-pregnene-3,20-dispiro-2',2'-di(1', 3'-thiazolidine-4'-hexyl carboxylate);

[27] 6α-Methyl-17α-acetyloxy-5-pregnene-3-spiro-2'-(1',3'-thiazolidine-4'-ethyl carboxylate)-20-one;

[28] 6α-Methyl-17α-acetyloxy-5-pregnene-3-spiro-2'-(1',3'-thiazolidine-4'-hexyl carboxylate)-20-one;

[29] 6α-Methyl-17α-acetyloxy-5-pregnene-3-spiro-2'-(1',3'-thiazolidine-4'-i-propyl carboxylate)-20-one;

[30] 5-Pregnene-3,20-dispiro-2',2'-di(1',3-thiazolidine-3'-ethoxycarbonyl-4'-ethyl carboxylate);

[31] 5-Pregnene-3,20-dispiro-2',2'-di(1',3'-thiazolidine-5',5'-dimethyl-4'-carboxylic acid); and

[32] 4-Pregnene-3,20-dispiro-2',2'-di(1',3'-thiazolidine-4'-ethyl carboxylate).

The compounds of the present invention are easily prepared, utilizing known techniques [compare generally our U.S. Pat. No. 4,069,322 assigned to the assignee hereof, the disclosure of which is hereby expressly incorporated by reference and relied upon]. Most conveniently, preparation involves contacting a compound corresponding to formula [I] but containing keto functions at C-3 and C-20 with a reagent of the formula

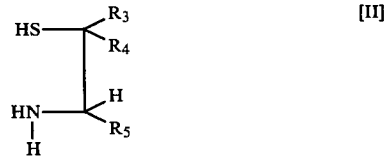

wherein $R_3$, $R_4$, and $R_5$ are as hereinbefore defined, in the presence of a suitable organic solvent (e.g., benzene, toluene, xylene, dimethylformamide, etc.) and further in the presence of a suitable organic base (e.g., trimethylamine, triethylamine, pyridine, etc.). This reaction is carried out at standard pressure, at a temperature of from room temperature to the boiling point of the solvent employed and for a period of time ranging from approximately 2 to 96 hours. In the course of this reaction, when the steroidal starting material is a $\Delta^4$ compound, the 4(5)-double bond can remain in its original position or migrate to the 5(6)-position, depending upon the particular reaction conditions employed.

The starting materials used in the preparation of the compounds of formula [I] can be prepared by known methods; thus, for example, the methods set forth in Examples I, II and III below are applicable to the preparation of various compounds of formula [II].

The invention will appear more fully from the examples which follow. These examples are given by way of illustration only and are not to be construed as limiting the invention either in spirit or in scope as many modifications both in materials and in methods will be apparent to those skilled in the art.

EXAMPLE I

Preparation of reactant L-cysteine butyl ester hydrochloride:

L-Cysteine hydrochloride 100 g was dissolved in 250 ml of butanol saturated with dry HCl. The solution was heated under reflux for 4 h. Excess of solvent was evaporated under evaporator. Ethyl acetate 150 ml was added to the residue to give crystals. Crystals were recrystallized from ethyl acetate, mp. 91° C., yield 30%, IR (KBr) 1745 cm$^{-1}$; NMR (CDCl$_3$) δ 9.2–8.4 (b, 3, NH$_3^\oplus$), 4.7 (t, 1, —CH), 4.3 (t, 2-, —CH$_2$)—, 3.3 (b, 2, CH$_2$S), 1.0 (t, 3, —CH$_3$—), 1.0–3.0 (m, 4, —CH$_2$CH$_2$).

Anal. Calcd for C$_7$H$_{16}$ClNO$_2$S: C, 39.33; H, 7.54; N, 6.55. Found: C, 39.70; H, 7.59; N, 6.50.

EXAMPLE II

Preparation of reactant L-cysteine hexyl ester hydrochloride:

L-Cysteine hydrochloride 78.5 g was added to 150 ml of hexanol saturated with dry HCl gas. The mixture was heated under reflux overnight. The solution was evaporated to about half of the total volume, ethyl ether 150 ml was added. The solution gave crystals when it was cooled. Crystals were filtered and were recrystallized from ethyl acetate; yield 45 g; mp 89°–90° C.; IR (KBr) 1745 cm$^{-1}$; NMR (CDCl$_3$) δ 9.2–8.4 (b, 3, NH$_3^\oplus$), 4.7 (5, 1, —CH—), 4.3 (t, 2, —OCH$_2$—), 3.4 (b, 2, CH$_2$S—), 1.0–3.0 (m, 8), 1.0 (t, 3-, CH$_5$).

EXAMPLE III

Preparation of reactant L-cysteine decyl ester hydrochloride:

L-Cysteine 157.4 g was added to 250 ml of decyl alcohol saturated with dry HCl. The mixture was heated to 150° for 6 h. The solution was cooled and was mixed with equal volume of ethyl acetate. The solution was cooled in a dry ice bath to give crystals. The crystals were filtered and were recrystallized from ethyl acetate, mp 96°–99° C., yield 100 g, IR (KBr) 1745 cm$^{-1}$; NMR (CDCl$_3$) δ.

Anal. Calcd for C$_{13}$H$_{28}$NClSO$_2$: C, 52.51; H, 9.49; N, 4.71. Found:

EXAMPLE IV

Preparation of 5-pregnene-3,20-dispiro-2',2'-di(1',3'-thiazolidine-4'-ethyl carboxylate):

Progesterone (6.3 g, 0.02 M) was dissolved in 50 ml of pyridine to which was added 13 g (0.07 Mole) of L-cysteine ethyl ester hydrochloride under a nitrogen atmosphere. After purging the system with nitrogen for 0.25 h, the reaction mixture was evaporated under vacuum. Methylene chloride, 100 ml, was added to precipitate excess of L-cysteine ethyl ester hydrochloride. The solution was filtered and the filtrate was evaporated to dryness. Ethanol 100 ml was added to the residue to give crystals. Crystals were recrystallized from ethyl acetate to give 4.5 g of desired product; mp 175° C.; IR (KBr) 1745 cm$^{-1}$ (s) (C=O); NMR (CDCl$_3$) δ 5.55–5.25 (m, 1, CH=C), 4.45–3.7 (m, 6, CH$_2$O and CH$_2$S), 3.7–2.3 (m, 6, CH$_2$S, CHN and NH); 1.57 (s, 3, CH —C(—S)—N), 1.03 (s, 3, CH$_3$—C), 0.85 (s, 3, CH$_3$C), 1.30 (t, 6, CH$_3$CH$_2$O), and 2.3–0.7 (m, 19, CH$_2$); [α]$^{26}$ D −70° (C=0.50, CHCl$_3$); TLC (silica gel, ether, R$_f$=0.50).

Anal. Calcd for C$_{31}$H$_{48}$N$_2$O$_4$S$_2$: C, 64.54; H, 8.39; N, 4.86. Found: C, 64.90; H, 8.35.

EXAMPLE V

Preparation of 5-pregnene-3,20-dispiro-2',2'-di(1',3'-thiazolidine-4'-butyl carboxylate):

Progesterone (6.3 g, 0.02 M) was dissolved in 50 ml of pyridine to which was added 20 g (0.094 M) of L-cysteine butyl ester hydrochloride. After purging the system with nitrogen for 0.25 h, the reaction mixture was stirred overnight at room temperature. Excess of pyridine was evaporated. The residue was dissolved in 150 ml of methylene chloride and the solution was washed with water 2×100 ml. The separated methylene chloride solution was dried over MgSO$_4$. After methylene chloride was evaporated, the residue was boiled with 150 ml of methanol. Crystals were filtered while the methanol solution was hot. Crystals were further recrystallized from ethanol to give the desired product; mp 149°–150° C., 2 g, IR (KBr) 1745 cm$^{-1}$ (s) (C=O); MNR (CDCl$_3$) δ 5.55–5.25 (m, 1, CH=C), 4.45–3.7 (m, 6, CH$_2$O, CH$_2$S)(m, 6, CH$_2$S, CHN, and NH), 1.57 (s, 3, CH$_3$—C(—S)-N), 1.03 (s, 3, CH$_3$C), 0.85 (s, 3, CH$_3$C) and 2.3–0.7 (m, 32, CH$_2$CH$_3$).

Anal. Calcd for C$_{35}$H$_{56}$N$_2$S$_2$O$_4$: C, 66.42; H, 8.92; N, 4.43. Found: C, 66.90; H, 9.20; N, 4.30.

EXAMPLE VI

Preparation of 5-pregnene-3,20-dispiro-2',2'-di(1',3'-thiazolidine-4'-hexyl carboxylate):

Progesterone (6.3 g, 0.02 M) was dissolved in 50 ml of pyridine to which was added 20 g (0.080 M) of L-cysteine hexyl ester hydrochloride. After purging the system with nitrogen for 0.25 h, the reaction mixture was stirred overnight at room temperature. The solution was mixed with 200 ml of ether. The ether solution was washed with 200 ml of water. The water solution was extracted with another 150 ml of ether. The combined ether solution was dried with MgSO$_4$. After the ether was evaporated, the residue was treated with 100 ml of methanol to give crystals after standing overnight. Crystals were recrystallized from ethanol to give 4 g of desired product, mp 113°–115° C.

Anal. Calcd for C$_{39}$H$_{64}$O$_4$S$_2$N$_2$: C, 67.98; H, 9.36; N, 4.07. Found: C, 68.40; H, 9.48; N, 3.90. IR (KBr) 1745 cm$^{-1}$ (s) (C=O); NMR (CDCl$_3$) δ 5.55–5.25 (m, 1, CH=C), 4.45–3.7 (m, CH$_2$O, CH$_2$S), 3.7–2.3 (m, 6, CH$_2$S, CHN and NH), 1.57 (s, 3, CH$_3$—C(—S)—N), 1.03 (s, 3, CH$_3$C), 0.85 (s, 3, CH$_3$C) and 2.3–0.7 (m, 40, CH$_2$) [α]$^{26}$D.

EXAMPLE VII

Preparation of 5-pregnene-3,20-dispiro-2',2'-di(1',3'-thiazolidine-4'-decyl carboxylate):

Progesterone (6.3 g, 0.02 M) was dissolved in 80 ml of pyridine to which was added 22 g (0.072 M) of L-cysteine decyl ester hydrochlorode. After purging the system with nitrogen for 0.25 h, the reaction mixture was stirred overnight at room temperature. Excess of pyridine was evaporated. The residue was dissolved in 150 ml of $CH_2Cl_2$ and the solution was washed with 500 ml of water. The organic layer was dried with $MgSO_4$. After the $CH_2Cl_2$ was evaporated, ethanol 100 ml was added to give crystals. Crystals were recrystallized from ethanol, mp 100°–102° C.; IR (KBr) 1745 cm$^{-1}$; NMR (CDCl$_3$) δ 5.55–5.25 (m, 1, CH=C); 4.45–3.7 (m, 6, CH$_2$O, CH$_2$S), 3.7–2.3 (m, 6, CH$_2$S, CHN and NH), 1.57 (s, 3, CH$_3$—C(S)—N), 1.03 (s, 3, CH$_3$C), 0.85 (s, 3, CH$_3$C) and 2.3–0.7 (m, 56, CH$_2$, CH$_3$).

Anal. Calcd for $C_{47}H_{80}N_2S_2O_4$: C, 70.45; H, 10.06; N, 3.50. Found: C, 70.62; H, 10.20; N, 3.40.

EXAMPLE VIII

Following those procedures and methods outlined in the foregoing Examples I to VII, but merely by substituting the appropriate specific reactants, the following additional compounds according to the invention are prepared:

5-Pregnene-3,20-dispiro-2',2'-di(1',3'-thiazolidine-4'-t-butyl carboxylate); 5-Pregnene-3,20-dispiro-2',2'-di(1',3'-thiazolidine-4'-benzyl carboxylate); 5-Pregnene-3,20-dispiro-2',2'-di(1',3'-thiazolidine-4'-i-propyl carboxylate); 5-Pregnene-3-spiro-2'-(1',3'-thiazolidine-4'-ethyl carboxylate)-20-one; 5-Pregnene-3-spiro-2'-(1',3'-thiazolidine-4'-butyl carboxylate)-20-one; 5-Pregnene-3-spiro-2'-(1',3'-thiazolidine-4'-hexyl carboxylate)-20-one; 5-Pregnene-3-spiro-2'-(1',3'-thiazolidine-4'-decyl carboxylate)-20-one; 5-Pregnene-3-spiro-2'-(1',3'-thiazolidine-4'-t-butyl carboxylate)-20-one; 5-Pregnene-3-spiro-2'-(1',3'-thiazolidine-4'-benzyl carboxylate)-20-one; 5-Pregnene-3-spiro-2'-(1',3'-thiazolidine-4'-i-propyl carboxylate)-20-one; 5-Pregnene-3,20-dispiro-2',2'-di(1',3'-thiazolidine-5',5'-dimethyl-4'-ethyl carboxylate); 5-Pregnene-3,20-dispiro-2',2'-di(1',3'-thiazolidine-5',5'-dimethyl-4'-hexyl carboxylate); 5-Pregnene-3,20-dispiro-2',2'-di(1',3'-thiazolidine-5',5'-dimethyl-4'-butyl carboxylate); 6α-Chloro-5-pregnene-3,20-dispiro-2',2'-di(1',3'-thiazolidine-4'-ethyl carboxylate); 6α-Chloro-5-pregnene-3,20-dispiro-2',2'-di(1',3'-thiazolidine-4'-butyl carboxylate); 6α-Chloro-5-pregnene-3,20-dispiro-2',2'-di(1',3'-thiazolidine-4'-hexyl carboxylate); 6α-Methyl-17α-acetyloxy-5-pregnene-3,20-dispiro-2',2'-di(1',3'-thiazolidine-4'-ethyl carboxylate); 6α-Methyl-17α-acetyloxy-5-pregnene-3,20-dispiro-2',2'-di(1',3'-thiazolidine-4'-butyl carboxylate); 6α-Methyl-17α-acetyloxy-5-pregnene-3,20-dispiro-2',2'-di(1',3'-thiazolidine-4'-hexyl carboxylate); 9α-Fluoro-17α-acetyloxy-5-pregnene-3,20-dispiro-2',2'-di(1',3'-thiazolidine-4'-ethyl carboxylate); 9α-Fluoro-17α-acetyloxy-5-pregnene-3,20-dispiro-2',2'-di(1',3'-thiazolidine-4'-butyl carboxylate); 9α-Fluoro-17α-acetyloxy-5-pregnene-3,20-dispiro-2',2'-di(1',3'-thiazolidine-4'-hexyl carboxylate); 6α-Methyl-17α-acetyloxy-5-pregnene-3-spiro-2'-(1',3'-thiazolidine-4'-ethyl carboxylate)-20-one; 6α-Methyl-17α-acetyloxy-5-pregnene-3-spiro-2'-(1',3'-thiazolidine-4'-hexyl carboxylate)-20-one; 6α-Methyl-17α-acetyloxy-5-pregnene-3-spiro-2'-(1',3'-thiazolidine-4'-i-propyl carboxylate)-20-one; 5-Pregnene-3,20-dispiro-2',2'-di(1',3'-thiazolidine-3'-ethoxycarbonyl-4'-ethyl carboxylate); and 5-Pregnene-3,20-dispiro-2',2'-di(1',3'-thiazolidine-5',5'-dimethyl-4'-carboxylic acid).

EXAMPLE IX

Preparation of 4-Pregnene-3,20-dispiro-2',2'-di(1',3'-thiazolidine-4'-ethyl carboxylate):

Cysteine ethyl ester hydrochloride (11.2 g, 0.06 mol) was suspended in 40 ml of triethylamine and stirred at room temperature for one hour. Filtration of the solid material gave a quantitative yield of triethylamine hydrochloride, with the purity of the salt being determined by ir. The excess triethylamine was evaporated from the solution under vacuum leaving cysteine ethyl ester as an oil. The purity of the ester was determined by nmr. The ester was added to 30 ml of pyridine solution containing progesterone (3.2 g, 0.01 mol) at room temperature and allowed to react for 3.5 days. The desired product precipitated from the reaction mixture as it was formed. Filtration of the solid followed by recrystallization from ethyl acetate gave 2.7 g (0.0047 mol, 47%) of the desired product; mp 162°–165° C., ir (KBr) 3460, 1740 cm$^{-1}$; nmr (CDCl$_3$) δ 5.2 (s, 1H, CH=C), 4.2 (q, 4H, CO$_2$CH$_2$CH$_3$), 4.2–3.6 (b, 2H), 1.5 (s, 3H, 21—C), 1.3 (t, 6H, CO$_2$CH$_2$CH$_3$), 1.0 (s, 3H, 18-C, (0.8 (s, 3H, 19-C), 3.6–0.6 (m, 26H) ppm; [α]$^{24.5°}$ =24.3° (C=0.63, CHCl$_3$).

EXAMPLE X

Following the procedure of Example IX, but substituting the appropriate specific reactants affords the following additional compounds of the invention:

4-pregnene-3,20-dispiro-2',2'-di(1',3'-thiazolidine-4'-butyl carboxylate); 4-pregnene-3,20-dispiro-2',2'-di(1',3'-thiazolidine-4'-hexyl carboxylate); 4-pregnene-3,20-dispiro-2',2'-di(1',3'-thiazolidine-4'-decyl carboxylate); 4-pregnene-3,20-dispiro-2'2'-di(1',3'-thiazolidine-4'-t-butyl carboxylate); 4-pregnene-3,20-dispiro-2',2'-di(1',3'-thiazolidine-4'-benzyl carboxylate); 4-pregnene-3,20-dispiro-2',2'-di(1',3'-thiazolidine-4'-i-propyl carboxylate); 4-pregnene-3-spirio-2'-(1',3'-thiazolidine-4'-ethyl carboxylate)-20-one; 4-pregnene-3-spiro-2'-(1',3'-thiazolidine-4'-butyl carboxylate)-20-one; 4-pregnene-3-spiro-2'-(1',3'-thiazolidine-4'-hexyl carboxylate)-20-one; 4-pregnene-3-spiro-2'-(1',3'-thiazolidine-4'-decyl carboxylate)-20-one; 4-pregnene-3-spiro-2'-(1',3'-thiazolidine-4'-benzyl carboxylate)-20-one; 4-pregnene-3-spiro-2'-(1',3'-thiazolidine-4'-t-butyl carboxylate)-20-one; 4-pregnene-3-spiro-2'-(1',3'-thiazolidine-4'-i-propyl carboxylate)-20-one; 4-pregnene-3,20-dispiro-2',2'-di(1',3'-thiazolidine-5',5'-dimethyl-4'-ethyl carboxylate); 4-pregnene-3,20-dispiro-2',2'-di(1',3'-thiazolidine-5',5'-dimethyl-4'-hexyl carboxylate); and 4-pregnene-3,20-dispiro-2',2'-di(1',3'-thiazolidine-5',5'-dimethyl-4'-butyl carboxylate).

The compounds of the present invention are conveniently administered via conventional topical administration with any suitable nontoxic pharmaceutically acceptable topical inert carrier material. Such carrier materials are well-known to those skilled in the art of topical pharmaceutical formulations. For those not skilled in the art, reference is made to the text entitled, "REMINGTON'S PHARMACEUTICAL SCIENCES", (Fourteenth Edition), 1970. Typical preparations for topical administration include lotions, creams, aerosols, ointments and gels containing the selected compound of formula (I) in combination with the conventional excipients. The preparation is simply applied topically to the afflicted area, whereby the therapeutically active compound is dermally absorbed and "cleaved" to release the parent steroid at the diseased site in an anti-acne or anti-seborrhea effective amount.

Naturally, the therapeutic dosage range for the compounds of the instant invention will vary with the size and needs of the patient, the potency of the parent steroidal compound, and the condition for which the compound is administered. A typical topical preparation for anti-acne use contains 0.01 to 5%, preferably 0.5 to 1%, of the prodrug. Application of 1 to 10 ml of lotion containing the aforementioned percentages of prodrug daily, or once every two days, to the affected areas will generally suffice. Less frequent application may also be possible in less severe cases or as therapy progresses and the acne condition improves.

The advantage of a representative prodrug of the present invention, namely, 5-pregnene-3,20-dispiro-2',2'-di(1',3'-thiazolidine-4'-ethyl carboxylate), over its parent steroid, progesterone, when applied topically is evident from the results of the test described below.

Female hairless mice, 10 to 12 weeks old and having a mean weight of 20 grams, were used. 17 μl of test solution was pipetted onto the pad of a Bandaid type test strip and the strip was carefully wrapped around the body of each mouse. The mice were kept for 24 hours in a metabolic cage, then were sacrificed and analyzed.

The progesterone test solution was prepared by dissolving 0.9 mg of progesterone in 675 μl of a 90:10 mixture of ethanol:isopropyl myristate thus resulting in a dose of 0.12 mg per mouse. The prodrug test solution was prepared by dissolving 1.85 mg of 5-pregnene-3,20-dispiro-2',2'-di(1',3'-thiazolidine-4'-ethyl carboxylate) in 675 μl of a 90:10 mixture of ethanol:isopropyl myristate resulting in a dose equivalent to 0.11 mg progesterone per mouse.

The results are tabulated below.

| Organ | Progesterone | | Prodrug | |
|---|---|---|---|---|
| | % Dose Mean ± S.E. | PPM/gm Organ Mean ± S.E. | % Dose Mean ± S.E. | PPM/gm Organ Mean ± S.E. |
| Feces | 16.65 ± 1.75 | 285,640 ± 26,870 | 0.95 ± 0.13 | 634 ± 930 |
| Urine | 7.00 1.14 | | 0.40 ± 0.09 | |
| Skin Circle | 1.98 ± 0.10 | 3,88 × 10⁵ ± | 4.52 ± 1.18 | 6.82 × 10⁵ ± 1.69 × 10⁵ |
| Int/Fat | 2.28 ± 0.47 | 71.840 ± 13,830 | 0.09 ± 0.00 | 2668 ± 295 |
| Liver | 0.75 ± 0.06 | 14,690 ± 2730 | 0.08 ± 0.01 | 1590 ± 225 |
| Blood | 0.08 ± 0.02 | | 0.28 ± 0.04 | 4080 ± 555 |
| Kidney/Spleen | 0.06 ± 0.01 | 3740 ± 290 | 0.03 ± 0.01 | 1430 530 |
| Lung | 0.04 ± 0.02 | 5560 ± 2100 | 0.01 ± — | 1740 ± 116 |
| Subtotal | 28.74 | | 6.36 | |
| Patch | 54.06 | | 83.46 ± 1.35 | |
| TOTAL | 82.80 | | 89.82 | |

The data show that the representative prodrug gives high concentration only in the skin, where it can exert its anti-acne or anti-seborrhea effect over a prolonged period without being systemically absorbed to any significant degree. In contrast, progesterone itself is rapidly absorbed through the skin and spreads throughout the body, significant amounts being detected in the feces, urine, fat and liver 24 hours after topical administration. Thus, topical administration of progesterone results in both rapid excretion of the active compound and concentration in body organs where its effect is not desired. In contrast, topical administration of the instant prodrugs affords high levels of the parent steroid in the skin without the significant systemic absorption and attendant side effects observed when the parent steroid itself is topically administered.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for topically treating acne or seborrhea on a subject afflicted with same which comprises topically administering thereto an anti-acne or anti-seborrhea effective amount of a compound having the formula

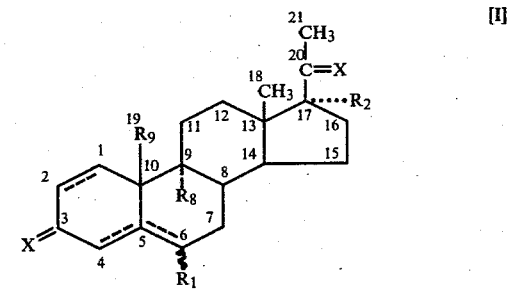

wherein each X is selected from the group consisting of 0 and

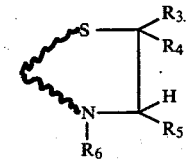

with the proviso that both X's cannot at the same time be 0, while either one or both can comprise the thiazolidine moiety;

$R_1$ is a member selected from the group consisting of H, $C_1$–$C_8$ alkyl and halogen;

$R_2$ is a member selected from the group consisting of H, OH, $OOCR_7$, halogen and $C_1$–$C_{10}$ alkyl;

R3 and R4 may be the same or different and each is selected from the group consisting of H and C1–C8 alkyl;

R5 is —COOR7;

R6 is a member selected from the group consisting of H, —COR7, —COOR7 and the pharmaceutically acceptable acid addition salts thereof;

R7 is a member selected from the group consisting of H, C1–C20 alkyl, C2–C20 alkenyl, C5–C7 cycloalkyl, C5–C7 cycloalkyl-aryl, phenyl and C1–C4 alkyl substituted phenyl;

R8 is a member selected from the group consisting of H, Cl and F; and

R9 is a member selected from the group consisting of H and C1–C8 alkyl.

2. A method for topically treating acne or seborrhea on a subject afflicted with same which comprises topically administering thereto an anti-acne or anti-seborrhea effective amount of a compound having the formula

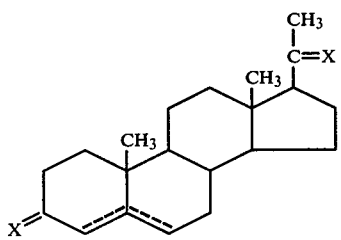

wherein each X is selected from the group consisting of O and

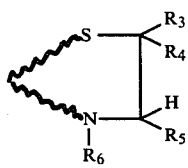

with the proviso that both X's cannot at the same time be O, while either one or both can comprise the thiazolidine moiety;

R3 and R4 may be the same or different and each is selected from the group consisting of H and C1–C8 alkyl;

R5 is —COOR7;

R6 is a member selected from the group consisting of H, —COR7, —COOR7 and the pharmaceutically acceptable acid addition salts thereof; and R7 is a member selected from the group consisting of H, C1–C20 alkyl, C2–C20 alkenyl, C5–C7 cycloalkyl, C5–C7 cycloalkyl-aryl, phenyl and C1–C4 alkyl substituted phenyl.

3. A method as defined by claim 1 or 2 wherein the X in the 3-position comprises the thiazolidine moiety and the X in the 20-position is oxygen.

4. A method as defined by claim 1 or 2 wherein the X in 20-position comprises the thiazolidine moiety and the X in the 3-position is oxygen.

5. A method as defined by claim 1 or 2 wherein each X comprises the thiazolidine moiety.

6. A method as defined by claim 1 or 2 wherein R6 is hydrogen.

7. A method as defined by claim 1 or 2 wherein R5 is —COOR7 wherein R7 is C1–C20 alkyl.

8. A pharmaceutical composition for topical use in the treatment of acne or seborrhea which comprises an anti-acne or anti-seborrhea effective amount of a compound having the formula

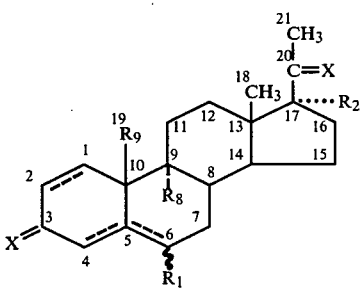

wherein each X is selected from the group consisting of O and

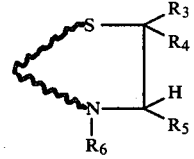

with the proviso that both X's cannot at the same time be O, while either one or both can comprise the thiazolidine moiety;

R1 is a member selected from the group consisting of H, C1–C8 alkyl and halogen;

R2 is a member selected from the group consisting of H, OH, OOCR7, halogen and C1–C10 alkyl;

R3 and R4 may be the same or different and each is selected from the group consisting of H and C1–C8 alkyl;

R5 is —COOR7;

R6 is a member selected from the group consisting of H, —COR7, —COOR7 and the pharmaceutically acceptable acid addition salts thereof;

R7 is a member selected from the group consisting of H, C1–C20 alkyl, C2–C20 alkenyl, C5–C7 cycloalkyl, C5–C7 cycloalkyl-aryl, phenyl and C1–C4 alkyl substituted phenyl;

R8 is a member selected from the group consisting of H, Cl and F; and

R9 is a member selected from the group consisting of H and C1–C8 alkyl; in combination with a pharmaceutically acceptable topical carrier material.

9. A pharmaceutical composition for topical use in the treatment of acne or seborrhea which comprises an anti-acne or anti-seborrhea effective amount of a compound having the formula

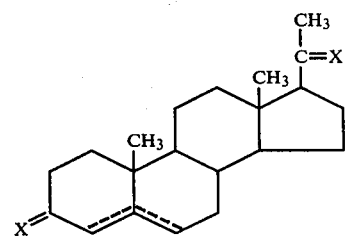

wherein each X is selected from the group consisting of O and

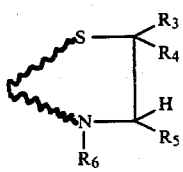

with the proviso that both X's cannot at the same time be 0, while either one or both can comprise the thiazolidine moiety;

$R_3$ and $R_4$ may be the same or different and each is selected from the group consisting of H and $C_1$–$C_8$ alkyl;

$R_5$ is —$COOR_7$;

$R_6$ is a member selected from the group consisting of H, —$COR_7$, —$COOR_7$ and the pharmaceutically acceptable acid addition salts thereof; and $R_7$ is a member selected from the group consisting of H, $C_1$–$C_{20}$ alkyl, $C_2$–$C_{20}$ alkenyl, $C_5$–$C_7$ cycloalkyl, $C_5$–$C_7$ cycloalkyl-aryl, phenyl and $C_1$–$C_4$ alkyl substituted phenyl; in combination with a pharmaceutically acceptable topical carrier material.

10. A composition as defined by claim 8 or 9 wherein the X in the 3-position comprises the thiazolidine moiety and the X in the 20-position is oxygen.

11. A composition as defined by claim 8 or 9 wherein the X in 20-position comprises the thiazolidine moiety and the X in the 3-position is oxygen.

12. A composition as defined by claim 8 or 9 wherein each X comprises the thiazolidine moiety.

13. A composition as defined by claim 8 or 9 wherein $R_6$ is hydrogen.

14. A composition as defined by claim 8 or 9 wherein $R_5$ is —$COOR_7$ wherein $R_7$ is $C_1$–$C_{20}$ alkyl.

15. A composition as defined by claim 9 wherein the compound of formula [II] is 5-pregnene-3,20-dispiro-2',2'-di(1',3'-thiazolidine-4'-ethyl carboxylate).

16. A composition as defined by claim 9 wherein the compound of formula [II] is 5-pregnene-3,20-dispiro-2',2'-di(1',3'-thiazolidine-4'-butyl carboxylate).

17. A composition as defined by claim 9 wherein the compound of formula [II] is 5-pregnene-3,20-dispiro-2',2'-di(1',3'-thiazolidine-4'-hexyl carboxylate).

18. A composition as defined by claim 9 wherein the compound of formula [II] is 5-pregnene-3,20-dispiro-2',2'-di(1',3'-thiazolidine-4'-decyl carboxylate).

19. A composition as defined by claim 9 wherein the compound of formula [II] is 5-pregnene-3,20-dispiro-2',2'-di(1',3'-thiazolidine-4'-t-butyl carboxylate).

20. A composition as defined by claim 9 wherein the compound of formula [II] is 5-pregnene-3,20-dispiro-2',2'-di(1',3'-thiazolidine-4'-benzyl carboxylate).

21. A composition as defined by claim 9 wherein the compound of formula [II] is 5-pregnene-3,20-dispiro-2',2'-di(1',3'-thiazolidine-4'-i-propyl carboxylate).

22. A composition as defined by claim 9 wherein the compound of formula [II] is 5-pregnene-3-spiro-2'-(1',3'-thiazolidine-4'-ethyl carboxylate)-20-one.

23. A composition as defined by claim 9 wherein the compound of formula [II] is 5-pregnene-3-spiro-2'-(1',3'-thiazolidine-4'-butyl carboxylate)-20-one.

24. A composition as defined by claim 9 wherein the compound of formula [II] is 5-pregnene-3-spiro-2'-(1',3'-thiazolidine-4'-hexyl carboxylate)-20-one.

25. A composition as defined by claim 9 wherein the compound of formula [II] is 5-pregnene-3-spiro-2'-(1',3'-thiazolidine-4'-decyl carboxylate)-20-one.

26. A composition as defined by claim 9 wherein the compound of formula [II] is 5-pregnene-3-spiro-2'-(1',3'-thiazolidine-4'-t-butyl carboxylate)-20-one.

27. A composition as defined by claim 9 wherein the compound of formula [II] is 5-pregnene-3-spiro-2'-(1',3'-thiazolidine-4'-benzyl carboxylate)-20-one.

28. A composition as defined by claim 9 wherein the compound of formula [II] is 5-pregnene-3-spiro-2'-(1',3'-thiazolidine-4'-i-propyl carboxylate)-20-one.

29. A composition as defined by claim 9 wherein the compound of formula [II] is 5-pregnene-3,20-dispiro-2',2'-di(1',3'-thiazolidine-5',5'-dimethyl-4'-ethyl carboxylate).

30. A composition as defined by claim 9 wherein the compound of formula [II] is 5-pregnene-3,20-dispiro-2',2'-di(1',3'-thiazolidine-5',5'-dimethyl-4'-hexyl carboxylate).

31. A composition as defined by claim 9 wherein the compound of formula [II] is 5-pregnene-3,20-dispiro-2',2'-di(1',3'-thiazolidine-5',5'-dimethyl-4'-butyl carboxylate).

32. A composition as defined by claim 9 wherein the compound of formula [II] is 5-pregnene-3,20-dispiro-2',2'-di(1',3'-thiazolidine-3'-ethoxycarbonyl-4'-ethyl carboxylate).

33. A composition as defined by claim 9 wherein the compound of formula [II] is 5-pregnene-3,20-dispiro-2',2'-di(1',3'-thiazolidine-5',5'-dimethyl-4'-carboxylic acid).

34. A composition as defined by claim 9 wherein the compound of formula [II] is 4-pregnene-3,20-dispiro-2',2'-di(1',3'-thiazolidine-4'-ethyl carboxylate).

35. A composition as defined by claim 9 wherein the compound of formula [II] is 4-pregnene-3,20-dispiro-2',2'-di(1',3'-thiazolidine-4'-butyl carboxylate).

36. A composition as defined by claim 9 wherein the compound of formula [II] is 4-pregnene-3,20-dispiro-2',2'-di(1',3'-thiazolidine-4'-hexyl carboxylate).

37. A composition as defined by claim 9 wherein the compound of formula [II] is 4-pregnene-3,20-dispiro-2',2'-di(1',3'-thiazolidine-4'-decyl carboxylate).

38. A composition as defined by claim 9 wherein the compound of formula [II] is 4-pregnene-3-spiro-2'-(1',3'-thiazolidine-4'-ethyl carboxylate)-20-one.

39. A composition as defined by claim 9 wherein the compound of formula [II] is 4-pregnene-3-spiro-2'-(1',3'-thiazolidine-4'-butyl carboxylate)-20-one.

40. A composition as defined by claim 9 wherein the compound of formula [II] is 4-pregnene-3-spiro-2'-(1',3'-thiazolidine-4'-hexyl carboxylate)-20-one.

41. A composition as defined by claim 9 wherein the compound of formula [II] is 4-pregnene-3-spiro-2'-(1',3'-thiazolidine-4'-decyl carboxylate)-20-one.

* * * * *